(12) United States Patent
Kartheus et al.

(10) Patent No.: US 6,616,793 B2
(45) Date of Patent: Sep. 9, 2003

(54) PRODUCTION OF MULTILAYERED THIN PLASTERS COMPRISING A CARRIER MATERIAL BASED ON POLYURETHANE

(75) Inventors: Holger Kartheus, Hamburg (DE); Andreas Beckmann, Hamburg (DE); Jürgen Christian Quandt, Klein Nordende (DE); Klaus Ruhnau, Barsbüttel (DE); Günther Sachau, Quickborn (DE); Thomas Möller, Hamburg (DE)

(73) Assignee: Beiersdorf AG, Hamburg (DE)

(*) Notice: Subject to any disclaimer, the term of this patent is extended or adjusted under 35 U.S.C. 154(b) by 0 days.

(21) Appl. No.: 09/957,222

(22) Filed: Sep. 20, 2001

(65) Prior Publication Data

US 2002/0104610 A1 Aug. 8, 2002

(30) Foreign Application Priority Data

Sep. 22, 2000 (DE) .......................................... 100 47 700

(51) Int. Cl.$^7$ .............................. B32B 31/20; B32B 7/12
(52) U.S. Cl. ..................... 156/289; 156/310; 156/323; 156/324; 264/175; 427/2.31
(58) Field of Search ................................. 156/182, 231, 156/237, 238, 241, 289, 310, 324, 323; 264/175; 427/2.31; 428/41.8, 42.3, 160, 220, 336

(56) References Cited

U.S. PATENT DOCUMENTS 4,499,896 A * 2/1985 Heinecke ...................... 602/47
5,974,974 A * 11/1999 Agnew et al. ............... 427/373

* cited by examiner

*Primary Examiner*—Richard Crispino
*Assistant Examiner*—Sing P. Chan
(74) *Attorney, Agent, or Firm*—Norris McLaughlin & Marcus

(57) ABSTRACT

A process for producing multilayered thin plasters with a carrier material based on polyurethane with the steps of applying at least one layer of uncured polyurethane to a transfer layer, applying an adhesive composition to a release layer, laminating the uncured polyurethane on the transfer layer and the adhesive composition on the release layer together using a doctor blade, passing the laminate through nip rolls downstream of the doctor blade, and rolled out the uncured polyurethane and adhesive composition to the ultimate thickness.

6 Claims, 1 Drawing Sheet

Figure 1:
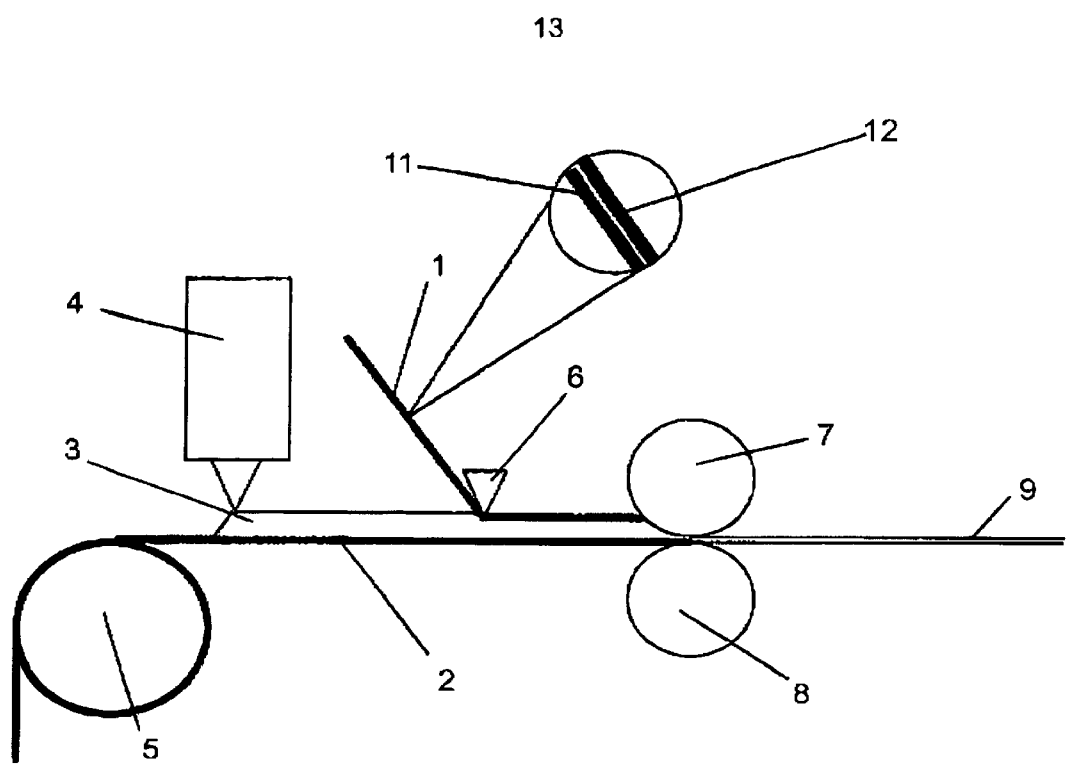

PRODUCTION OF MULTILAYERED THIN PLASTERS COMPRISING A CARRIER MATERIAL BASED ON POLYURETHANE

This invention relates to a process for producing multilayered thin plasters comprising a carrier material based on polyurethane.

BACKGROUND OF THE INVENTION

Multilayered thin plasters comprising a carrier material based on polyurethane are customarily produced by the polyurethane composition being spread coated on a carrier material and being laminated together with an adhesive composition, preferably likewise a polyurethane, using a doctor blade before it has cured. It has hitherto not been possible to produce very thin carrier layers of polyurethane. This is because when the doctor blade gap is set to a very low height, although it produces a thin polyurethane layer, the high viscosity of the polyurethane causes a buildup of material upstream of the doctor blade. This buildup of reactive polyurethane becomes blocked in time, rendering continuous operation impossible.

Foam wound contact materials as obtainable for example from Beiersdorf under the name of Cutinova® thin and Cutinova® hydro will be used by way of example to explain the production process in more detail. They are described inter alia in DE 42 33 289 A1, in DE 196 18 825 A1 and WO 97/43328.

According to these references, the polyurethane gel foam consists of a polyaddition product of a polyetherpolyol (Levagel® from Bayer AG) with an aromatic or aliphatic diisocyanate (Desmodur® Bayer AG), into which a polyacrylate superabsorbent powder (Favor®, Stockhausen) has been incorporated. The polyurethane gel can be made weakly or strongly self-adherent to skin depending on the ratio of OH equivalents of the polyol to reactive isocyanate groups.

The sheetlike polyurethane gel foam from 1 to 6 mm in thickness is covered by a polyurethane film on one side upstream of a doctor blade. Plasters of appropriate size are punched out of the bale material.

The punched-out large-area wound contact materials are very useful for managing chronic or slow-healing wounds of patients who have to be treated in hospital.

It is an object of the present invention to provide a process capable of producing very thin, single- or multilayered plasters comprising a polyurethane carrier in a continuous operation.

SUMMARY OF THE INVENTION

The invention accordingly provides a process for producing multilayered thin plasters comprising a carrier material based on polyurethane, which comprises a) applying at least one layer of a polyurethane to a transfer, b) applying an adhesive composition to a release layer, c) laminating the uncured polyurethane on the transfer and the adhesive composition on the release layer together using a doctor blade in particular, d) passing the laminate downstream of the doctor blade into a roll nip in which the polyurethane and the adhesive composition are rolled out to the ultimate thickness.

DETAILED DESCRIPTION

In a first advantageous embodiment of the process, the roll nip is formed by two smooth rolls.

In a further preferred embodiment, the roll nip is formed by a top embossing roll and a smooth bottom roll.

The embossing makes it possible, first, to adjust the polyurethane layer on the moving carrier web to the desired thickness and, secondly, to create specific accumulations of material in the coherent polyurethane layer in order that plasters of any shape may be punched out as a result.

The embossing roll may comprise various embossments to provide a change in the polyurethane layer. These embossments may have the shape of a semiconcave lens for example, This leads to raised centers in the polyurethane layer, which are beveled off toward the edge. Other possibilities include ellipsoids, cuboids, cubes or other geometric shapes in order that specific shapes may be created in the PU layer.

For example, in the case of the lens, the result is a polyurethane layer which, after punching, is beveled off from a point in the center toward the edge.

This point is situated In the area's middle in particular in order that a symmetrical appearance may be obtained for the beveled layer. But the beveling may also be irregular, depending on the requirements and application scenario of the plaster.

The height of the edge zone is not more than 50% of the overall height of the product, preference being given to edge zone heights of less than 0.2 mm. The contouring profile from the center to the edge is defined by the mold chosen, i.e, the casting mold determines the design of the contour.

To provide the desired thickness reduction, the roll nip preferably generates a pressure of at least 4 bar, especially 5 bar.

The polyurethane layer, furthermore, preferably has a post roll nip thickness of 10 to 100 $\mu$m, especially 40 to 60 $\mu$m.

The adhesive, furthermore, preferably has a post roll nip thickness of 20 to 100 $\mu$m, especially 40 to 60 $\mu$m.

The carrier film preferably comprises a transparent multilayered moisture vapor pervious polyurethane, polyethylene, polypropylene, polyamide or polyester film. But this enumeration is not to be understood as conclusive in that, it will be appreciated, one skilled in the art is able to come up with other suitable films without inventive step. In an advantageous embodiment, these films have a thickness of 10 to 100 $\mu$m, especially 40 to 60 $\mu$m.

The advantageous thickness results from the need for a flexurally stiff material which resists curling when subjected to mechanical loading.

In a further advantageous embodiment, it comprises a skin friendly pressure sensitive adhesive composition comprising polyacrylate into which a tackifier (a hydrocarbon resin for example) is incorporated to enhance the adhesion to skin.

The release layer is preferably a release paper which has been siliconized on one side.

The polyurethane layer is in particular transparent, highly moisture vapor pervious and adhesive. To store fluid, it is preferable to incorporate a superabsorbent polymer as a powder.

The polyurethane layer serves as good cushioning and as a storage medium for exudate from the wound.

Useful polyurethanes form part of the subject matter of DE 196 18 825, which discloses hydrophilic, self-adhesive polyurethane gels consisting of a) polyetherpolyols with 2 to 6 hydroxyl groups and having OH values of 20 to 112 and an ethylene oxide (EO) content of $\geq$10 weight %, b) antioxidants,
c) bismuth(III) carboxylates soluble in the polyols a) and based on carboxylic acids having 2 to 18 carbon atoms as catalysts and also
d) hexamethylene diisocyanate.

wherein the product of the functionalities of the polyurethane-forming components a) and d) is at least 5.2, the quantity of catalyst c) amounts to 0.005 to 0.25 weight %, relative to the polyol a), the quantity of antioxidants b) is in the range from 0.1 to 1.0 weight %, based on polyol a), and the ratio of free NCO groups of component d) to the free OH groups of component a) (isocyanate index) is selected within the range from 0.30 to 0.70.

Preference is given to using polyetherpolyols having 3 to 4, most preferably 4, hydroxyl groups and an OH number in the range from 20 to 112, preferably 30 to 56. The ethylene oxide content in the polyetherpolyols used according to the invention is preferably ≧20% by weight.

Polyetherpolyols are known per se and are prepared for example by polymerization of epoxides, such as ethylene oxide, propylene oxide, butylene oxide or tetrahydrofuran, with themselves or by addition of these epoxides, preferably of ethylene oxide and propylene oxide—optionally mixed with each other or separately in succession—to starter components having at least two reactive hydrogen atoms, such as water, ethylene glycol, propylene glycol, diethylene glycol, dipropylene glycol, glycerol, trimethylolpropane, pentaerythritol, sorbitol or sucrose. Representatives of the useful high molecular weight polyhydroxy compounds mentioned are recited for example in High Polymers, Vol. XVI, "Polyurethanes, Chemistry and Technology" (Saunders-Frisch, Interscience Publishers, New York, volume 1, 1962, pages 32–42).

The isocyanate component used is monomeric or trimerized hexamethylene diisocyanate or hexamethylene diisocyanate modified by biuret, uretidione, allophanate groups or by prepolymerization with polyetherpolyols or mixtures of polyetherpolyols based on the known starter components with 2 or >2 reactive hydrogen atoms and epoxides, such as ethylene oxide or propylene oxide having an OH number of ≦850, preferably 100 to 600. Preference is given to the use of modified hexamethylene diisocyanate, especially hexamethylene diisocyanate modified by prepolymerization with polyetherdiols of OH number 200 to 600. Very particular preference is given to modifications of hexamethylene diisocyanate with polyetherdiols of OH number 200–600 whose residual level of monomeric hexamethylene diisocyanate is below 0.5% by weight.

Useful catalysts for the polyurethane gels of the invention are bismuth(III) carbonates which are soluble in the water-free polyetherpolyols a) and are based on linear, branched, saturated or unsaturated carboxylic acids having 2 to 18, preferably 6 to 18, carbon atoms. Preference is given to Bi(III) salts of branched saturated carboxylic acids having tertiary carboxyl groups, such as 2,2-dimethyloctanoic acid (for example Versatic acids, Shell). Of particular suitability are formulations of these Bi(III) salts in excess fractions of these carboxylic acids. Of outstanding utility is a solution of 1 mol of the Bi(III) salt of Versatic 10 acid (2,2-dimethyloctancic acid) in an excess of 3 mol of this acid with a Bi content of about 17%.

The catalysts are preferably used in amounts from 0.03 to 0.1% by weight, based on polyol a).

Useful antioxidants for the polyurethane gels of the invention are in particular sterically hindered phenolic stabilizers, such as BHT (2,6-ditert-butyl4-methylphenol). Vulkanox BKF (2,2'-methylenebis(6-tert-butyl-4-methylphenol) (Bayer AG), Irganox 1010 (pentaerythrityl tetrakis-[3-(3,5-ditert-butyl4-hydroxyphenyl)propionate]), Irganox 1076 (octadecyl 3-(3,5-ditert-butyl-4-hydroxyphenyl)propionate) (Ciba-Geigy) or tocopherol (vitamin E). Preference is given to using those of the α-tocopherol type.

The antioxidants are preferably used in amounts from 0.15 to 0.5% by weight, based on polyol a).

The isocyanate index (ratio of the free NCO groups used in the reaction to the free OH groups) of the polyurethane gel compositions according to the invention is in the range from 0.30 to 0.70, preferably in the range from 0.45 to 0.60, depending on the functionality of the isocyanate and polyol components used. The isocyanate index required for gel formation is very simple to estimate by the following formula:

$$f_{(polyol)} \cdot (f_{(isocyanate)} - 1) \cdot \text{index} \approx 2$$

$$\text{index} \approx \frac{2}{f_{(polyol)} \cdot (f_{(isocyanate)} - 1)}$$

f: functionality of isocyanate or polyol component

Depending on the tackiness or elasticity required of the gel, the isocyanate index to be actually used may differ from the calculated value by up to +20%.

The polyurethane gel compositions of the invention are prepared by customary processes as described for example in Becker/Braun, Kunststoff-Handbuch, volume 7, Polyurethanes pages 121 ff, Carl-Hauser, 1983.

Preference is further given to the use of polyurethanes as disclosed in EP 0 665 856 B1. The hydrophilic polyurethane gel foams are accordingly obtainable from
1. a polyurethane gel which comprises
   (A) 25–62% by weight, preferably 30–60% by weight, particularly preferably 40–57% by weight, based on the sum total of (A) and (B), of a covalently crosslinked polyurethane as a high molecular weight matrix and
   (B) 75–38% by weight, preferably 70–40% by weight, particularly preferably 60–43% by weight, based on the sum total of (A) and (B), of one or more polyhydroxy compounds which are firmly held in the matrix by secondary valence forces and have an average molecular weight between 1000 and 12,000, preferably between 1500 and 8000, particularly preferably between 2000 and 6000, and an average OH number between 20 and 112, preferably between 25 and 84, particularly preferably between 28 and 56, as a liquid dispersant, the dispersant being substantially free of hydroxy compounds having a molecular weight below 800, preferably below 1000, particularly preferably below 1500, and optionally
   (C) 0 to 100% by weight, based on the sum total of (A) and (B), of filler and/or additive substances, and which is obtainable by reaction of a mixture of
      a) one or more polyisocyanates,
      b) one or more polyhydroxy compounds having an average molecular weight between 1000 and 12,000 and an average OH number of between 20 and 112,
      c) optionally catalysts or accelerants for the reaction between isocyanate groups and hydroxyl groups and also optionally
      d) filler and additive substances known per se from polyurethane chemistry,
wherein this mixture is substantially free of hydroxy compounds having a molecular weight below 800, the average functionality of the polyisocyanates ($F_1$) is between 2 and 4, the average functionality of the polyhydroxy compound ($F_p$) is between 3 and 6 and the isocyanate index (K) conforms to the formula $$K = \frac{300 \pm X}{(F_I \cdot F_p) - 1} + 7$$

where X is $\leq 120$, preferably X is $\leq 100$, particularly preferably X is $\leq 90$, and the index K has values between 15 and 70, the specified molecular weight and OH number averages being number averages, 2. a water absorbent material and
3. a nonaqueous foaming agent.

The polyurethane gels are preparable from the starting compounds known per se from polyurethane chemistry by processes known per se as described for example in DE 31 03 499 A1, DE 31 03 500 A1 and EP 0 147 588 A1. It is essential, however, that the above-defined conditions be adhered to for the selection of the gel-forming components, or nontacky, elastic gels will be obtained Instead of self-adhesive gels.

Preferred polyhydroxy compounds are polyetherpolyols as more particularly specified in the abovementioned laid-open specifications.

Useful polyisocyanate components Include not only (cyclo)aliphatic but also aromatic isocyanates. Preferred (cyclo)aliphatic polyisocyanates are 1,6-hexamethylene diisocyanate and also its biurets and trimers and hydrogenated diphenylmethane diisocyanate ("MDI") grades. Preferred aromatic polyisocyanates are those which are obtained by distillation, such as MDI mixtures of 4,4'- and 2,4'-isomers or 4,4'-MDI, and also toluyene diisocyanate ("TDI") grades.

The diisocyanates can be selected in particular for example from the group of the unmodified aromatic or aliphatic diisocyanates or else from modified products formed by prepolymerization with amines, polyols or polyetherpolyols.

The polyurethane composition may be unfoamed, foamed, unfilled or filled with additional fillers, for example superabsorbents, titanium dioxide, zinc oxide, plasticizers, dyes, etc. For applications in the field of transdermal plaster systems, it is also possible to dope the polyurethane composition in the central zone with active substances. Furthermore, it is possible to use hydrogels in solid to semisolid form with active constituents for the central zone.

The polyurethane gels may optionally contain additives known per se from polyurethane chemistry, for example fillers and short fibers based on inorganics or organics, metal pigments, surface-active substances or liquid extenders such as substances having a boiling point of above 150° C.
Useful organic fillers include for example barite, chalk, gypsum, kieserite, sodium carbonate, titanium dioxide, cerium oxide, quartz sand, kaolin, carbon black and microballoons.
Useful organic fillers include for example powders based on polystyrene, polyvinyl chloride, urea-formaldehyde and polyhydrazodicarbonamide. Useful short fibers include for example glass fibers 0.1–1 mm in length or fibers of organic origin such as for example polyester or polyamide fibers. Metal powders, for example iron or copper powder, can likewise also be used in gel formation. To confer the desired color on the gels, it is possible to use the organic or inorganic dyes or color pigments known per se for the coloration of polyurethanes, for example iron oxide or chromium oxide pigments, phthalocyanine- or monoazo-based pigments.

Useful surface-active substances include for example cellulose powders active carbon and silica products.

To modify the adhesive properties of the gels, they may optionally include adds of polymeric vinyl compounds, polyacrylates and other copolymers customary in adhesive technology or else adhesives based on natural materials up to a level of 10% by weight, based on the weight of the gel composition.

Preferred water-absorbing materials are the water-absorbing salts known as superabsorbents, of polyacrylates and copolymers thereof, especially the sodium or potassium salts. They may be crosslinked or uncrosslinked and are also obtainable as commercial products. Particularly suitable products are those disclosed in DE 37 13 601 A1 and also new-generation superabsorbents with only low remaining contents of water which can be dried out and high swelling capacity under pressure. Preferred products are lightly crosslinked polymers based on acrylic acid/sodium acrylate. Such sodium polyacrylates are obtainable as Favor 22-SK (Chemische Fabrik Stockhausen GmbH, Germany). Further absorbents are likewise suitable, for example carboxymethylcellulose and karaya.

The degree of foaming can be varied within wide limits through the incorporated amounts of foaming agent.

If appropriate, the self-adhesive product is covered up by a siliconized paper or a, particularly siliconized, film, so that the adhesive side is protected during storage.

The process of the invention provides thin PU plasters comprising a polyurethane composition as wound contact material in one operation.

The preferred process variant with the embossed roll even provides products having very to extremely thin edges.

It has hitherto been known to fabricate plasters whose polyurethane carriers have a basis weight of 120 g/m$^2$ to 150 g/m$^2$. It is now possible to provide minimal basis add-ons of less than 30 g/m$^2$.

In what follows, an illustration will be used to describe a particularly advantageous inventive process for producing multilayered thin plasters comprising a carrier material based on polyurethane.

BRIEF DISCUSSION OF THE DRAWING

FIG. 1 illustrates a preferred embodiment of the process of the invention.

The first step comprises a layer of polyurethane 11 being applied to a transfer layer 12. Concurrently, an adhesive composition 3 is applied to a release layer 2. To this end, the release layer 2 is moved via a roll 5 to underneath a container 4 from which the adhesive composition 3 is applied in a certain layer thickness to the release layer 2.

The compositum 1 of uncured polyurethane 11 and transfer 12 is laminated together with the adhesive composition 3 on the release layer 2 using a doctor blade 6 and fed to a roll nip formed by the two rolls 7 and 8.
In the roll nip, the polyurethane 11 and the adhesive composition 3 are rolled out to the ultimate thickness.

The roll nip can be formed by two smooth rolls 7, 8 but the top roll 7 can also be an embossing roll.

What is claimed is:

1. A process for producing multilayered thin plasters comprising a carrier material based on polyurethane, which comprises
   a) applying at least one layer of an uncured polyurethane to a transfer layer,
   b) applying an adhesive composition to a release layer,
   c) laminating the uncured polyurethane on the transfer layer and the adhesive composition on the release layer together using a doctor blade, d) passing the laminate downstream of the doctor blade into a roll nip in which the polyurethane and the adhesive composition are rolled out to the ultimate thickness.

2. The process of claim 1, wherein the roll nip is formed by two smooth rolls.

3. The process of claim 1, wherein the roll nip is formed by a top embossing roll and a smooth bottom roll.

4. The process of claim 1, 2 or 3, wherein the roll nip generates a pressure of at least 4 bar.

5. The process of, claim 1, 2 or 3, wherein the polyurethane layer has a post roll nip thickness of 10 to 100 $\mu$m.

6. The process of claim 1, 2 or 3, wherein the adhesive has a post roll nip thickness of 20 to 100 $\mu$m.

* * * * *

UNITED STATES PATENT AND TRADEMARK OFFICE
CERTIFICATE OF CORRECTION

PATENT NO. : 6,616,793 B2
DATED : September 9, 2003
INVENTOR(S) : Kartheus et al.

It is certified that error appears in the above-identified patent and that said Letters Patent is hereby corrected as shown below:

Column 8,
Lines 1, 3 and 5, "claim" should read -- claims --

Signed and Sealed this

Twenty-first Day of June, 2005

JON W. DUDAS
*Director of the United States Patent and Trademark Office*